United States Patent
Saikou et al.

(10) Patent No.: US 11,120,554 B2
(45) Date of Patent: Sep. 14, 2021

(54) IMAGE DIAGNOSIS APPARATUS, IMAGE DIAGNOSIS METHOD, AND PROGRAM

(71) Applicant: NEC Corporation, Tokyo (JP)

(72) Inventors: Masahiro Saikou, Tokyo (JP); Hitoshi Imaoka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 94 days.

(21) Appl. No.: 16/487,136

(22) PCT Filed: Feb. 28, 2017

(86) PCT No.: PCT/JP2017/007782
§ 371 (c)(1),
(2) Date: Aug. 20, 2019

(87) PCT Pub. No.: WO2018/158817
PCT Pub. Date: Sep. 7, 2018

(65) Prior Publication Data
US 2019/0370971 A1  Dec. 5, 2019

(51) Int. Cl.
*G06T 7/00* (2017.01)
*G06T 7/90* (2017.01)
(Continued)

(52) U.S. Cl.
CPC .............. *G06T 7/0016* (2013.01); *A61B 1/04* (2013.01); *G06T 7/20* (2013.01); *G06T 7/60* (2013.01);
(Continued)

(58) Field of Classification Search
CPC ........... G06T 7/0016; G06T 7/90; G06T 7/20; G06T 7/60; G06T 2207/10016;
(Continued)

(56) References Cited

U.S. PATENT DOCUMENTS

| | | | |
|---|---|---|---|
| 2006/0189843 | A1 | 8/2006 | Nakamura et al. |
| 2014/0085686 | A1 | 3/2014 | Ishihara |
| 2014/0184790 | A1 | 7/2014 | Ishihara |
| 2018/0092518 | A1 | 4/2018 | Yaguchi |

FOREIGN PATENT DOCUMENTS

| | | | |
|---|---|---|---|
| JP | 2005-124965 A | 5/2005 | |
| JP | 2007-209770 A | 8/2007 | |

(Continued)

OTHER PUBLICATIONS

Machine translation for JP 2011-156203, IDS (Year: 2011).*

(Continued)

*Primary Examiner* — Qian Yang
(74) *Attorney, Agent, or Firm* — Sughrue Mion, PLLC

(57) ABSTRACT

An image diagnosis apparatus (10) performs a diagnosis assistance process using images (moving image) generated by an endoscope or the like. The image diagnosis apparatus (10) includes a first processing unit (110) and a second processing unit (120). The first processing unit (110) executes preprocessing of deciding whether or not a tumor judgment process is necessary with respect to each of a plurality of input images. The second processing unit (120) performs the tumor judgment process with respect to the input image for which it is decided that "the tumor judgment process is necessary" in the preprocessing executed by the first processing unit (110).

21 Claims, 13 Drawing Sheets

(51) Int. Cl.
*A61B 1/04* (2006.01)
*G06T 7/20* (2017.01)
*G06T 7/60* (2017.01)

(52) U.S. Cl.
CPC ...... *G06T 7/90* (2017.01); *G06T 2207/10016* (2013.01); *G06T 2207/10068* (2013.01); *G06T 2207/30096* (2013.01); *G06T 2207/30101* (2013.01); *G06T 2207/30168* (2013.01)

(58) Field of Classification Search
CPC ........... G06T 2207/10068; G06T 2207/30096; G06T 2207/30101; G06T 2207/30168; A61B 1/04; A61B 1/00009
See application file for complete search history.

(56) References Cited

FOREIGN PATENT DOCUMENTS

| | | |
|---|---|---|
| JP | 2011-156203 A | 8/2011 |
| JP | 2012-249804 A | 12/2012 |
| JP | 2013-056040 A | 3/2013 |
| JP | 2016-154810 A | 9/2016 |
| WO | 2016/208001 A1 | 12/2016 |

OTHER PUBLICATIONS

Japanese Office Action for JP Application No. 2019-502319 dated Aug. 11, 2020 with English Translation.
International Search Report for PCT Application No. PCT/JP2017/007782, dated May 23, 2017.

* cited by examiner

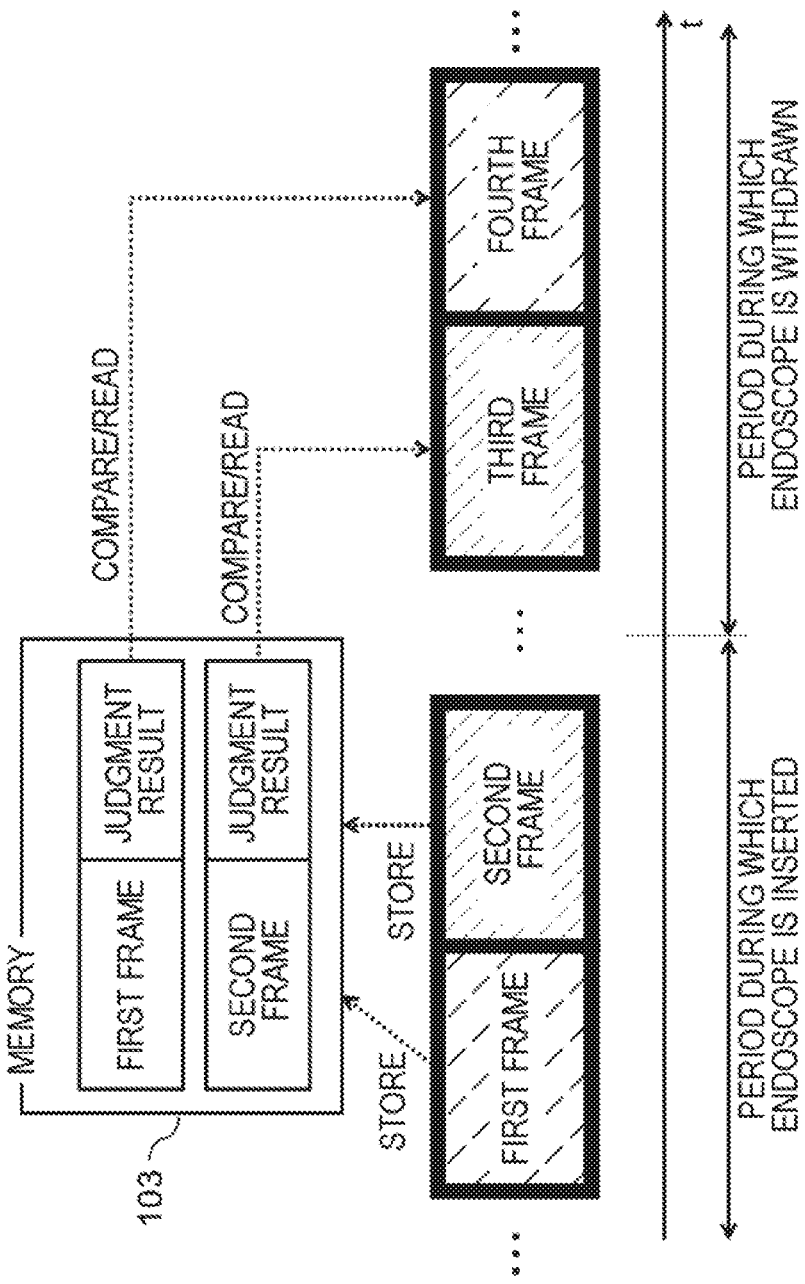

IMAGE DIAGNOSIS APPARATUS, IMAGE DIAGNOSIS METHOD, AND PROGRAM

This application is a National Stage Entry of PCT/JP2017/007782 filed on Feb. 28, 2017, the contents of all of which are incorporated herein by reference, in their entirety.

TECHNICAL FIELD

The present invention relates to an image diagnosis apparatus, an image diagnosis method, and a program.

BACKGROUND ART

A technology which assists a diagnosis of a tumor using a moving image which is acquired through an endoscope is disclosed in, for example, Patent Document 1 and Patent Document 2 below. Patent Document 1 below discloses a technology which sets a Region Of Interest (ROI) with respect to an endoscope image so as to perform display that assists the diagnosis through the endoscope on the basis of an image feature value in the ROI. Patent Document 2 below discloses a technology which enables a doctor to perform enlargement imaging on an anxious part using the endoscope having an ultra-enlargement function so as to determine whether or not the part corresponds to the tumor using the image.

RELATED DOCUMENT

Patent Document

[Patent Document 1] Japanese Patent Application Publication No. 2007-209770
[Patent Document 2] Japanese Patent Application Publication No. 2016-154810

SUMMARY OF THE INVENTION

Technical Problem

In a case where tumor diagnosis assistance is performed by processing an image acquired using an endoscope, there is a possibility that a requested performance is not satisfied as in a case where a load on image processing for judging a tumor is large and thus display misalignment is generated.

The present invention is made in consideration of the above problem. One object of the present invention is to provide a technology which reduces a throughput in the tumor diagnosis assistance using the image.

Solution to Problem

An image diagnosis apparatus of the present invention includes (1) a first processing unit that executes preprocessing of deciding whether or not a tumor judgment process is necessary with respect to each of a plurality of input images, and (2) a second processing unit that performs the tumor judgment process with respect to the input image for which it is decided in the preprocessing that the tumor judgment process is necessary.

An image diagnosis method of present invention is executed by a computer. The image diagnosis method includes (1) executing preprocessing of deciding whether or not a tumor judgment process is necessary with respect to each of a plurality of input images, and (2) performing the tumor judgment process with respect to the input image for which it is decided in the preprocessing that the tumor judgment process is necessary.

According to the present invention, there is provided a program causing a computer to execute the image diagnosis method according to the present invention.

Advantageous Effects of Invention

According to the present invention, there is provided a technology which reduces a throughput in tumor diagnosis assistance using an image.

BRIEF DESCRIPTION OF THE DRAWINGS

The above-described object, other objects, features, and advantages will be further apparent with preferable example embodiments, which will be described below, and the accompanying drawings below.

FIG. 13 is a diagram illustrating a modification example of the third example embodiment.

DESCRIPTION OF EMBODIMENTS

Hereinafter, example embodiments of the present invention will be described with reference to the accompanying drawings. Also, the same symbols are attached to the same components throughout the drawings, and the description thereof will not be repeated. In addition, unless description is particularly performed, each block in each block diagram indicates a configuration in a functional unit instead of a configuration in a hardware unit.

<Outline>

Figure 1:
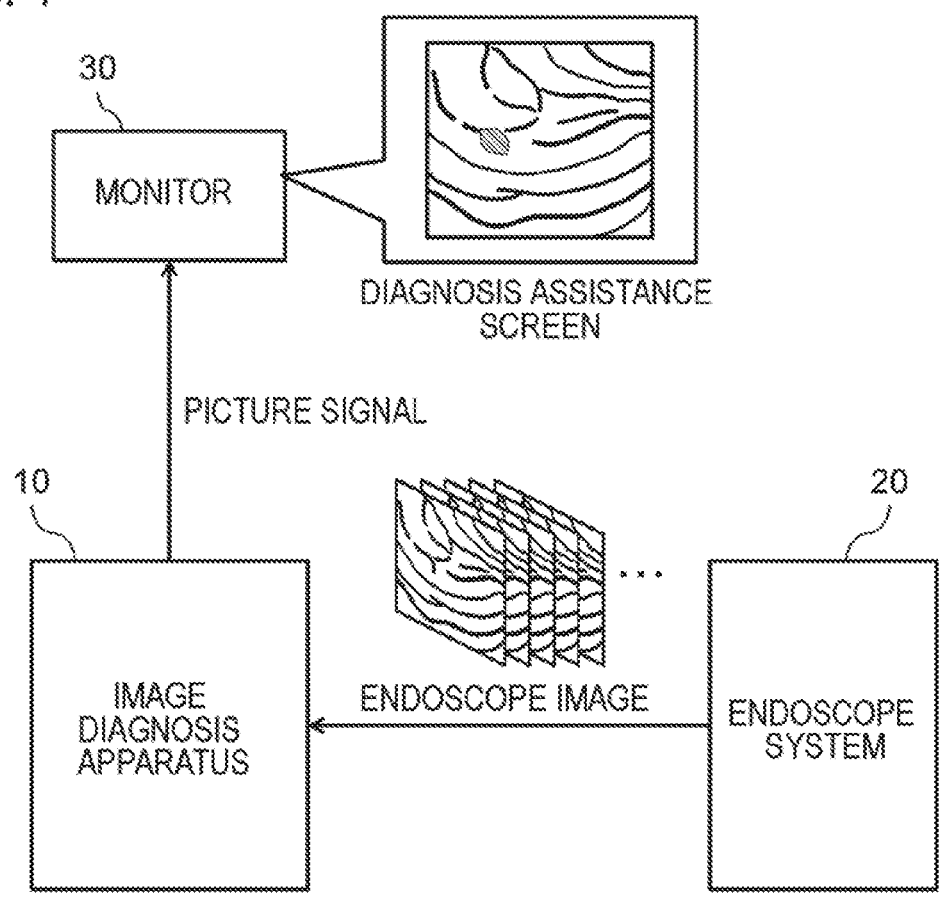
FIG. 1 is a diagram illustrating an introduction example of an image diagnosis apparatus according to the present invention.

FIG. 1 is a diagram illustrating an introduction example of an image diagnosis apparatus according to the present invention. As illustrated in FIG. 1, an image diagnosis apparatus 10 according to the present invention is connected to an endoscope system 20 and a monitor 30. It should be noted that, the image diagnosis apparatus 10 may be incorporated in the endoscope system 20 as one element of the endoscope system 20.

The endoscope system 20 is a system which is used to assist a diagnosis and a therapy using an endoscope, and includes a videoscope (endoscope), a control apparatus which controls the videoscope, a processor which processes a signal acquired from the videoscope and generates an endoscope image, and the like. By inserting the videoscope into the interior of the body of a patient from a mouth or a nose of the patient, an image (moving image) which is acquired by imaging the interior of the body of the patient is generated.

The image, which is generated by the endoscope system 20, is supplied to the image diagnosis apparatus 10. The image diagnosis apparatus 10 performs a tumor judgment process using the image (moving image) generated by the endoscope system 20, and generates a picture signal for displaying a diagnosis assistance screen (a screen which is used to prevent a tumor from being overlooked by displaying information such as existence or non-existence of the tumor and a type of the tumor in a distinguishable manner) which shows a result of the judgment process. Here, as will be described in detail below, the image diagnosis apparatus 10 reduces a throughput and speeds up the process by sorting images which are input from the endoscope system 20 into an image which is a target of the judgment process, and an image which is not the target of the judgment process.

The monitor 30 displays the diagnosis assistance screen on the basis of the picture signal which is output from the image diagnosis apparatus 10. A doctor performs a diagnosis while checking the information of the existence or non-existence of the tumor and the type of the tumor over the diagnosis assistance screen which is displayed on the monitor 30.

First Example Embodiment

Hereinafter, the image diagnosis apparatus 10 according to the present invention will be described.

[Functional Configuration]

Figure 2:
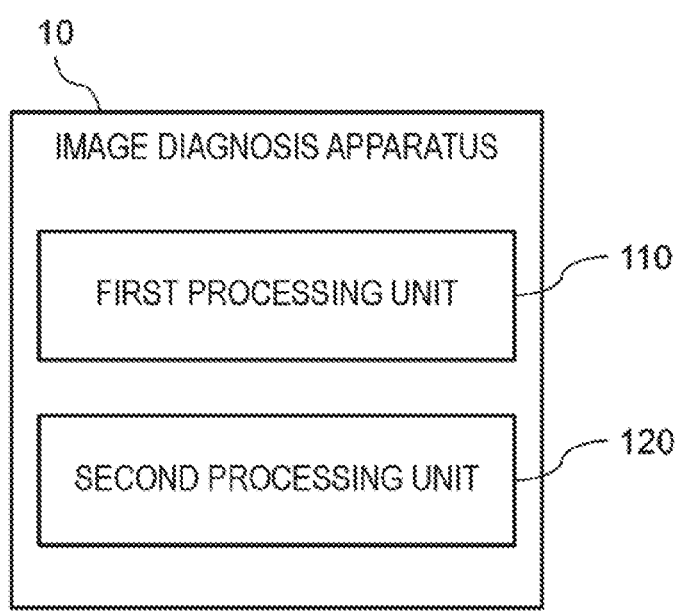
FIG. 2 is a block diagram schematically illustrating a functional configuration of an image diagnosis apparatus according to a first example embodiment.

FIG. 2 is a block diagram schematically illustrating a functional configuration of an image diagnosis apparatus 10 according to a first example embodiment. As illustrated in FIG. 2, the image diagnosis apparatus 10 includes a first processing unit 110 and a second processing unit 120.

The first processing unit 110 acquires a plurality of input images as processing targets. The plurality of input images are, for example, frames which are included in a moving image generated by the endoscope system 20. It is possible for the first processing unit 110 to acquire the moving image (the plurality of input images), which is generated when a diagnosis is performed using the endoscope system 20, in real time. In addition, after the diagnosis using the endoscope system 20 ends, the first processing unit 110 may read the moving image (the plurality of input images), which is first stored in an image storage apparatus of the endoscope system 20, from the image storage apparatus.

The first processing unit 110 executes preprocessing of deciding whether or not the tumor judgment process is necessary with respect to each of the plurality of acquired input images. The preprocessing, which is executed by the first processing unit 110, will be described in detail below. The plurality of input images are sorted into images on which the judgment process is executed, and images on which the judgment process is not executed, through the preprocessing which is executed by the first processing unit 110.

It is possible for the first processing unit 110 to decide "whether or not the tumor judgment process with respect to the input images is necessary" on the basis of, for example, a point of view of "whether or not the doctor is observing". As an example, a case where movement between the input images acquired by the first processing unit 110 is small corresponds to a case where the doctor is not largely moving the endoscope, and thus it is possible to decide that the doctor is observing a part included in an imaging range. In this case, it is possible for the first processing unit 110 to decide that "the tumor judgment process with respect to the input images is necessary". On the other hand, in a case where the movement between the input images acquired by the first processing unit 110 is large, the doctor is largely moving the endoscope, and thus it is possible to decide that the doctor is not observing the part included in the imaging range. In this case, it is possible for the first processing unit 110 to decide that "the tumor judgment process with respect to the input images is not necessary".

In addition, it is possible for the first processing unit 110 to decide "whether or not the tumor judgment process is necessary with respect to the input images" on the basis of, for example, a point of view of "whether or not the doctor notices the tumor". As an example, in a case where it is possible to decide that the doctor is performing any treatment with respect to the tumor (that is, the doctor notices the tumor) from the input images, it is possible for the first processing unit 110 to decide that "the tumor judgment process with respect to the input images is not necessary". On the other hand, in a case where it is not possible to check that the doctor is performing any treatment with respect to the tumor from the input images, there is a possibility that the doctor does not notice the tumor. In this case, it is possible for the first processing unit 110 to decide that "the tumor judgment process with respect to the input images is necessary".

In addition, it is possible for the first processing unit 110 to decide "whether or not the tumor judgment process is necessary" on the basis of, for example, a point of view of "evasion of execution of the redundant judgment process". As an example, in a case where there is a small change in a certain input image (first input image) compared to an input image (second input image) in the past, it is possible for the first processing unit 110 to decide that "the tumor judgment process with respect to the first input image is not necessary". The decision is based on the following consideration. That is, in a case where there is the small change in the image as a result of comparison performed on the plurality of input images, it is possible to estimate that the input images are acquired by imaging approximately the same place. If so, it may be mentioned that a result of a case where the tumor judgment process is executed with respect to each of the input images is approximately the same. That is, since it is possible to apply a result of the second input image to the first input image, it may be mentioned that it is not necessary to execute the tumor judgment process with respect to the first input image.

In addition, it is possible for the first processing unit 110 to decide "whether or not the tumor judgment process is necessary" on the basis of, for example, a point of view of "whether or not the input image is suitable for the tumor judgment process". As an example, in a case where the input image is not clear and it is possible to decide that it is difficult to acquire an accurate process result, it is possible for the first processing unit 110 to decide that "the tumor judgment process with respect to the input images is not necessary".

It should be noted that, the description about a reference of the decision of "whether or not the tumor judgment process is necessary" is just an example, and does not limit the present invention.

The second processing unit 120 performs the tumor judgment process with respect to the input image for which it is decided that "the tumor judgment process is necessary" in the preprocessing performed by the first processing unit 110, using various feature values which can be extracted from the input image. Specifically, the second processing unit 120 first judges existence or non-existence of the tumor in an imaging range of the input image using the various feature values which can be extracted from the input image. In a case where it is decided that the tumor exists, the second processing unit 120 judges a character (positive (malignant)/negative (benign)) of the tumor on the basis of the various feature values which can be extracted from the input image.

As an example, it is possible for the second processing unit 120 to decide whether the result of the tumor judgment process is positive or negative on the basis of at least one of a color and a shape of a blood vessel which appears on the inside wall of an organ in the input image. It is possible for the second processing unit 120 to judge whether the tumor is any of positive or negative using a color change pattern of a blood vessel part in the input image, a shape pattern on the basis of an edge feature value of the blood vessel part in the input image, and the like. In addition, as another example, it is possible to decide whether the result of the tumor judgment process is any of positive or negative on the basis of a shape of the inside wall of the organ in the input image. It is possible for the second processing unit 120 to decide whether the result of the tumor judgment process is any of positive or negative on the basis of the edge feature value of a tumor part which appears on the inside wall of the organ in the input image.

It should be noted that, in the specification, "to judge whether positive or negative" is to acquire not only information related to the character (positive/negative) of the tumor but also, for example, another information, which is useful for the diagnosis, such as a location of the tumor within the input image, a size of the tumor, a type of the tumor, and a degree of progression (stage number) of the tumor. Hereinafter, these pieces of information are also expressed as "diagnosis assistance information".

Advantageous Effects

Hereinabove, according to the example embodiment, through the preprocessing performed by the first processing unit 110, the plurality of input images are sorted into images on which the tumor judgment process by the second processing unit 120 is necessary, and images on which the tumor judgment process by the second processing unit 120 is not necessary. The tumor judgment process using the images is a process which requires relatively large load. Therefore, in a case where the images corresponding to the processing targets are thinned out, an effect is expected in which a throughput of a whole process relating to the diagnosis assistance decreases. Therefore, the diagnosis assistance process is speeded up. For example, even in a case where the endoscope images are processed in real time, it is possible to smoothly output results. In addition, specification requested from the apparatus used for the diagnosis assistance process is lowered, and thus an effect is also expected in which an introduction cost for the diagnosis assistance system using the endoscope image decreases.

Hereinafter, the example embodiment will be described in further detail.

[Hardware Configuration of Image Diagnosis Apparatus 10]

Each of functional configuration units of the image diagnosis apparatus 10 may be realized by hardware (for example: a hard-wired electronic circuit, or the like) which realizes each functional configuration unit, or may be realized by a combination of hardware and software (for example: a combination of an electronic circuit and a program which controls the electronic circuit, or the like). Hereinafter, a case where each functional configuration unit of the image diagnosis apparatus 10 is realized by the combination of hardware and software will be further described.

Figure 3:
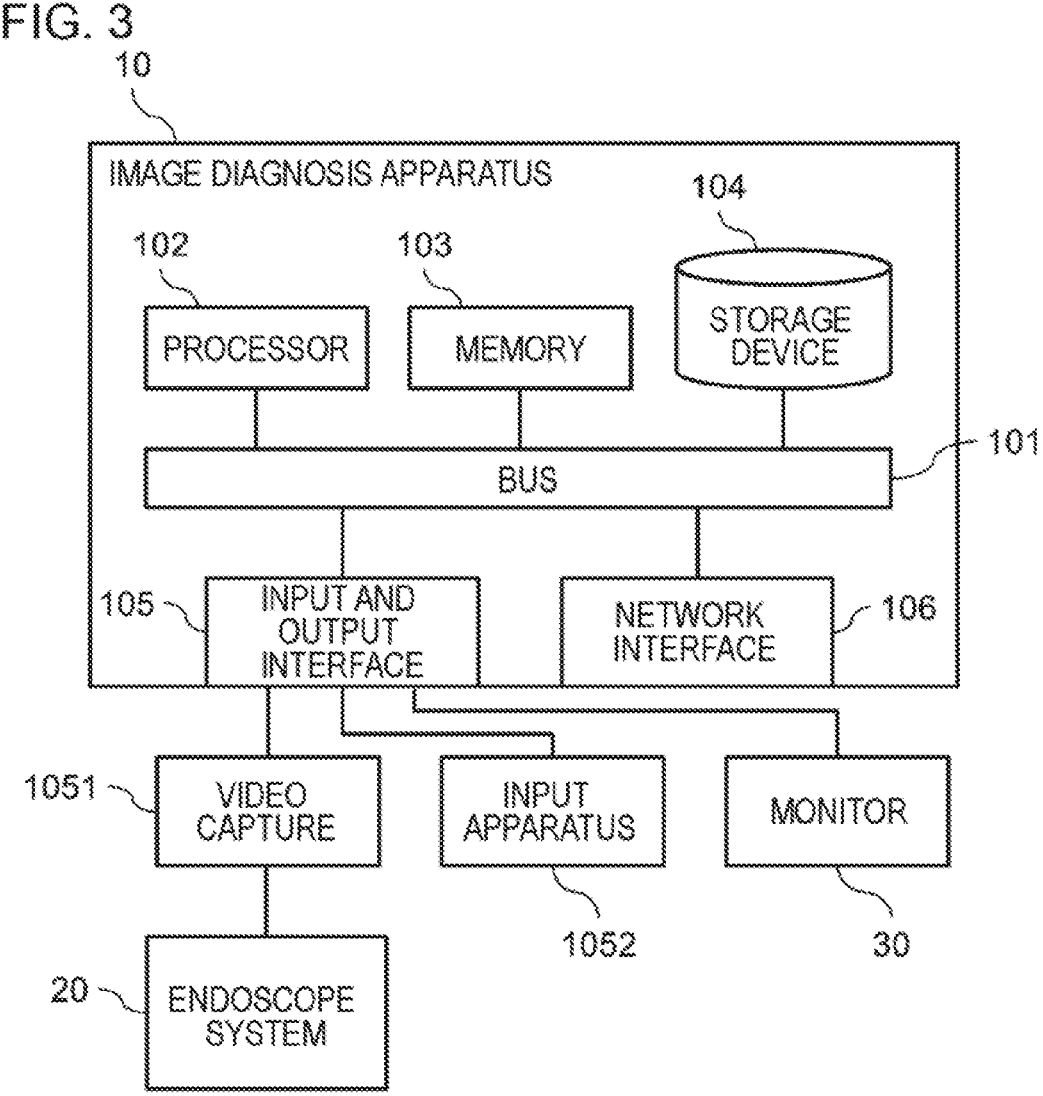
FIG. 3 is a diagram conceptually illustrating a hardware configuration of the image diagnosis apparatus.

FIG. 3 is a diagram conceptually illustrating a hardware configuration of the image diagnosis apparatus 10. The image diagnosis apparatus 10 is, for example, a computer, such as a server machine.

The image diagnosis apparatus 10 includes a bus 101, a processor 102, a memory 103, a storage device 104, an input and output interface 105, and a network interface 106. The bus 101 is a data transmission path which is used for the processor 102, the memory 103, the storage device 104, the input and output interface 105, and the network interface 106 to transmit and receive data to and from each other. However, a method for connecting the processor 102, the memory 103, the storage device 104, the input and output interface 105, the network interface 106, and the like to each other is not limited to bus connection.

The processor 102 is an arithmetic processing unit such as a Central Processing Unit (CPU) or a Graphics Processing Unit (GPU). The memory 103 is a main storage apparatus which is realized using a Random Access Memory (RAM), a Read Only Memory (ROM), or the like. The storage device 104 is an auxiliary storage apparatus which is realized using a Hard Disk Drive (HDD), a Solid State Drive (SSD), a memory card, or the like.

The storage device 104 stores program modules which realize functional configuration units (the first processing unit 110 and the second processing unit 120) of the image diagnosis apparatus 10. The processor 102 realizes functions corresponding to the program modules by fetching and executing the program modules in the memory 103.

The input and output interface 105 is an interface which is used to connect the image diagnosis apparatus 10 to peripheral devices for input and output. In an example of FIG. 3, the image diagnosis apparatus 10 is connected to the monitor 30, a video capture 1051, and an input apparatus 1052 through the input and output interface 105. In addition, a foot switch (not illustrated in the drawing), which performs a screen switching operation or the like, may be further connected to the input and output interface 105.

The monitor 30 includes a Liquid Crystal Display (LCD), a Cathode Ray Tube (CRT) display, or the like. The monitor 30 displays the diagnosis assistance screen (for example: the diagnosis assistance screen of FIG. 1) on the basis of the picture signal which is output through the input and output interface 105 and which is processed by the processor 102 of the image diagnosis apparatus 10.

The video capture 1051 is connected to the endoscope system 20. The video capture 1051 encodes the endoscope image (moving image) which is generated in the endoscope system 20, and transmits the encoded endoscope image to the image diagnosis apparatus 10.

The input apparatus 1052 includes, for example, a mouse, a keyboard, or the like. The input apparatus 1052, such as the mouse or the keyboard, may be integrated with the monitor 30 as the touch panel.

The network interface 106 is an interface which is used to connect the image diagnosis apparatus 10 to various communication networks. The communication network includes, for example, a Local Area Network (LAN), a Wide Area Network (WAN), and the like. A method for connecting the network interface 106 to the communication network may be wireless connection or wired connection.

It should be noted that, the image diagnosis apparatus 10 may be realized by a plurality of apparatuses. For example, it is possible to realize the first processing unit 110 and the second processing unit 120 of the image diagnosis apparatus 10 using a plurality of apparatuses which are different from each other. In this case, storage devices of the apparatuses may store program modules corresponding to the functional configuration units realized in the apparatuses.

Operation Example

Figure 4:
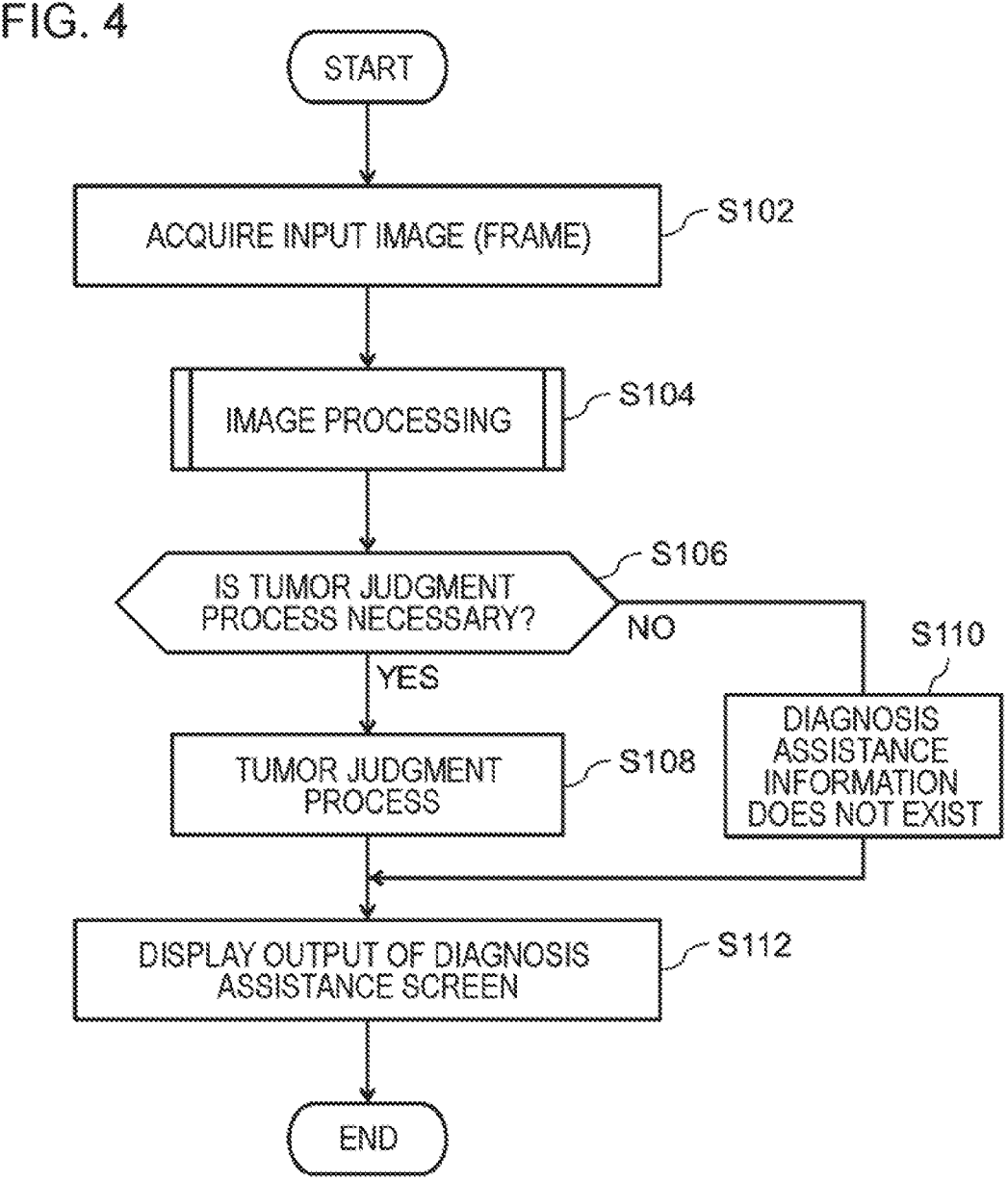
FIG. 4 is a flowchart illustrating a flow of a process performed by the image diagnosis apparatus according to the first example embodiment.

Hereinafter, an operation example of the image diagnosis apparatus 10 according to the first example embodiment will be described with reference to FIG. 4. FIG. 4 is a flowchart illustrating a flow of a process performed by the image diagnosis apparatus 10 according to the first example embodiment.

The first processing unit 110 acquires an input image (frame) based on the endoscope image (moving image) generated by the endoscope system 20 (S102).

Furthermore, the first processing unit 110 executes image processing with respect to the input image acquired in S102 (S104), and decides a necessity of the tumor judgment process, which is performed by the second processing unit 120, on the basis of a result of the image processing (S106). The processes in S104 and S106 correspond to preprocessing.

In a case where the first processing unit 110 decides that "the tumor judgment process is necessary" (S106: YES), the second processing unit 120 executes the tumor judgment process with respect to the input image which is acquired in S102 (S108). Furthermore, the second processing unit 120 generates the picture signal, which is used to display the diagnosis assistance screen, using the diagnosis assistance information which is acquired as a result of the process in S108, and outputs the picture signal to the monitor 30 (S112).

On the other hand, in a case where the first processing unit 110 decides that "the tumor judgment process is not necessary" (S106: NO), the second processing unit 120 skips the tumor judgment process with respect to the input image which is acquired in S102. In this case, the first processing unit 110 recognizes that "the diagnosis assistance information does not exist" (S110), and outputs the input image, which is acquired from the endoscope system 20, to the monitor 30 without change (S112).

<Preprocessing Performed by First Processing Unit 110>

The preprocessing performed by the first processing unit 110 will be described in detail. The first processing unit 110 decides whether or not a condition (hereinafter, also expressed as "determination condition"), which is previously set, is detected in the image processing with respect to the input image acquired in S102, as the preprocessing. In a case where the determination condition is detected in the preprocessing, the first processing unit 110 decides that "the tumor judgment process performed by the second processing unit 120 is not necessary".

Hereinafter, a specific example of the preprocessing, which is executed by the first processing unit 110, will be described with reference to FIGS. 5 to 10.

First Specific Example

Figure 5:
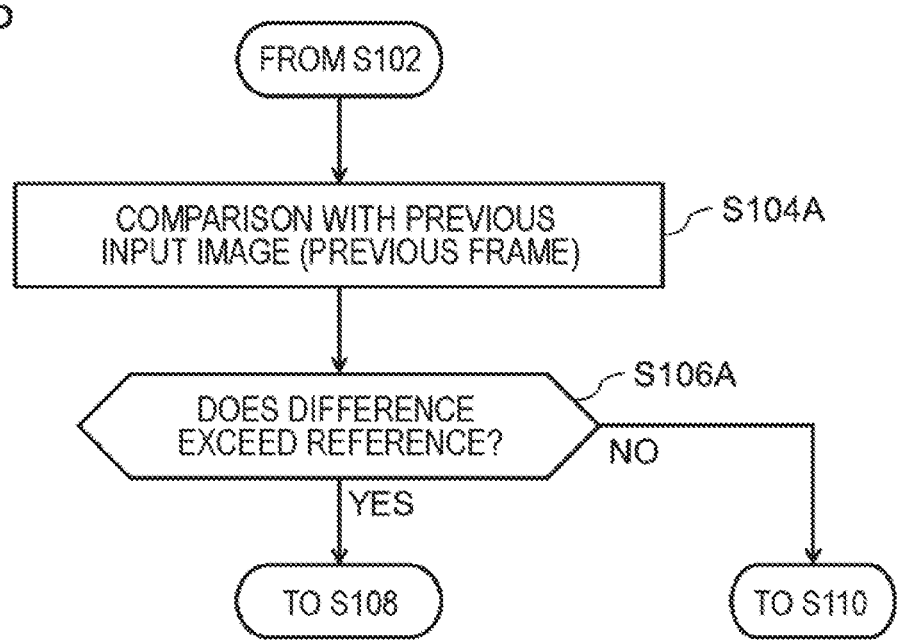
FIG. 5 is a flowchart illustrating a first specific example of preprocessing executed by a first processing unit.

FIG. 5 is a flowchart illustrating a first specific example of the preprocessing which is executed by the first processing unit 110. In the specific example, the first processing unit 110 detects that "a difference between two successive input images as the frames, which are included in the moving image, is equal to or less than a reference" as the determination condition. In a case where the difference is small which is acquired as a result of a comparison of a certain input image and a previous input image thereof, the two input images are similar to each other, and thus it is possible to apply a result of the tumor judgment with respect to the previous input image without change. With respect to the input image, it may be mentioned that the tumor judgment process is not necessary. On the other hand, in a case where the difference is large which is acquired as the result of the comparison of the certain input image and the previous input image thereof, the two input images are not similar to each other, and thus it is not possible to apply the result of the tumor judgment with respect to the previous input image without change. With respect to the input image, it may be mentioned that the tumor judgment process is necessary.

The first processing unit 110 compares the input image (the first input image) acquired in S102 with the previous input image (for example, an immediately before frame) of the first input image (S104A). It is possible for the first processing unit 110 to judge a similarity between the two input images by comparing, for example, indexes such as color histogram and a binary pattern of respective pixels in the images. It should be noted that, the second input image is input to the image diagnosis apparatus 10 prior to the first input image, and is maintained in, for example, the memory 103 or the storage device 104. It is possible for the first processing unit 110 to acquire the second input image by accessing the memory 103 or the storage device 104.

Furthermore, the first processing unit 110 decides whether or not the difference between the two input images exceeds the reference on the basis of a result of the comparison in S104A (S106A).

Specifically, it is possible for the first processing unit 110 to decide whether or not the difference between the two input images exceeds the reference by performing a process as follows. First, the first processing unit 110 calculates a score, which indicates a degree of the similarity or a degree of the difference, by comparing indexes, such as the color histogram and the binary pattern of the respective pixels, between the two input images. The first processing unit 110 compares a reference value, which is previously maintained in the memory 103 or the like, with the calculated score. For example, in a case where the score which indicates the degree of the similarity is calculated and the score exceeds the reference value, the first input image is similar to the second input image in the past, and thus it is possible for the first processing unit 110 to decide that "the tumor judgment process is not necessary". In addition, for example, in a case where the score which indicates the degree of the difference is calculated and the score is equal to or less than the reference value, the first input image is similar to the second input image in the past, and thus it is possible for the first processing unit 110 to decide that "the tumor judgment process is not necessary".

A case where it is decided that "the difference between the two input images exceeds the reference" in the decision in S106A (S106A: YES) is, in other words, a case where the determination condition is not detected. In this case, the first processing unit 110 decides that "the tumor judgment process with respect to the first input image is necessary", and instructs the second processing unit 120 to execute the tumor judgment process with respect to the first input image. The second processing unit 120 executes the tumor judgment process with respect to the input image, which is acquired in S102, according to the instruction (S108).

On the other hand, a case where it is decided that the difference between the two input images is equal to or less than the reference" in the decision in S106A (S106A: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

Second Specific Example

Figure 6:
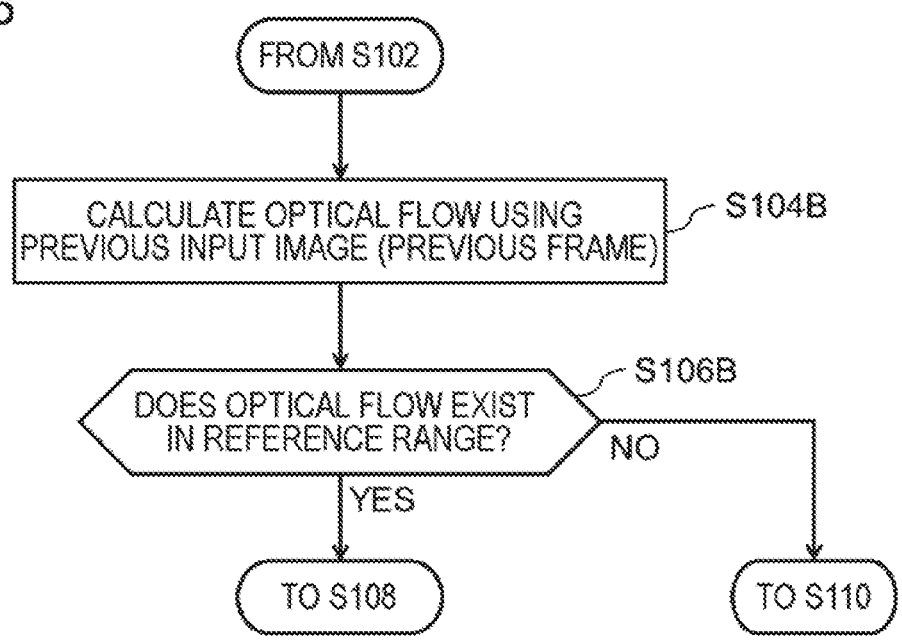
FIG. 6 is a flowchart illustrating a second specific example of the preprocessing executed by the first processing unit.

FIG. 6 is a flowchart illustrating a second specific example of the preprocessing which is executed by the first processing unit 110. In the specific example, the first processing unit 110 detects that "an optical flow which is calculated using the plurality of input images is out of a reference range" as the determination condition. In a case where an input image which has a large optical flow (movement vector) compared to the previous input image is acquired, it is possible to decide that the doctor is largely moving the endoscope and is not observing the part included in the imaging range. It is possible to decide that the tumor judgment process is not necessary with respect to the input image. In addition, in a case where an input image which has a small optical flow (movement vector) compared to the previous input image, is acquired, it is possible to decide that the doctor is hardly moving the endoscope and is observing the part included in the imaging range. It is possible to decide that the tumor judgment process is necessary with respect to the input image.

The first processing unit 110 uses the input image (first input image) acquired in S102 and the input image (for example, the immediately before frame) which is previous to the first input image and thus calculates the optical flow (movement vector) between the input images (S104B). It should be noted that, the second input image is input to the image diagnosis apparatus 10 prior to the first input image, and is maintained in, for example, the memory 103 or the storage device 104. It is possible for the first processing unit 110 to access the memory 103 or the storage device 104, and to acquire the second input image.

Furthermore, the first processing unit 110 decides whether or not the optical flow (movement vector) calculated in S104B exists in the reference range (S106B). Specifically, the first processing unit 110 reads the reference range, which is previously maintained, in the memory 103 or the like. The reference range is defined using, for example, a first threshold and a second threshold. It is possible for the first processing unit 110 to judge whether or not the optical flow (movement vector) calculated in S104B exists in the reference range by comparing the optical flow (movement vector) with each of the first threshold and the second threshold.

Here, the first threshold is a threshold which is used to decide whether or not the doctor is observing. It is possible to set the first threshold on the basis of, for example, a change value in the frames according to an average insertion speed or withdrawal speed of the endoscope during observation. In addition, the second threshold is set to a value which is less than the first threshold. As illustrated in FIG. 5, the second threshold is a threshold which is used to decide whether or not the difference between the two input images is equal to or less than the reference value.

In a case where the optical flow (movement vector) calculated in S104B exceeds the first threshold, it is possible to decide that the doctor is not observing the part included in the imaging range. In this case, it is possible for the first processing unit 110 to decide that "the tumor judgment process with respect to the input images is not necessary". In addition, in a case where the optical flow (movement vector) calculated in S104B is equal to or less than the first threshold, it is possible to decide that the doctor is observing the part included in the imaging range. In this case, it is possible for the first processing unit 110 to decide that "the tumor judgment process with respect to the input images is necessary". It should be noted that, in a case where the optical flow (movement vector) calculated in S104B is equal to or less than the second threshold, it is possible to decide that the change in the image is small even though the doctor is observing the part included in the imaging range. In this case, it is possible for the first processing unit 110 to decide that "the tumor judgment process with respect to the input images is not necessary".

A case where it is decided that "the optical flow is in the reference range" in the decision in S106B (S106B: YES) is, in other words, a case where the determination condition is not detected. In this case, the first processing unit 110 decides that "the tumor judgment process with respect to the first input image is necessary", and instructs the second processing unit 120 to execute the tumor judgment process with respect to the first input image. The second processing unit 120 executes the tumor judgment process with respect to the input images acquired in S102 according to the instruction (S108).

On the other hand, a case where it is decided that the "optical flow is out of the reference range" in the decision in S106B (S106B: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

Third Specific Example

Figure 7:
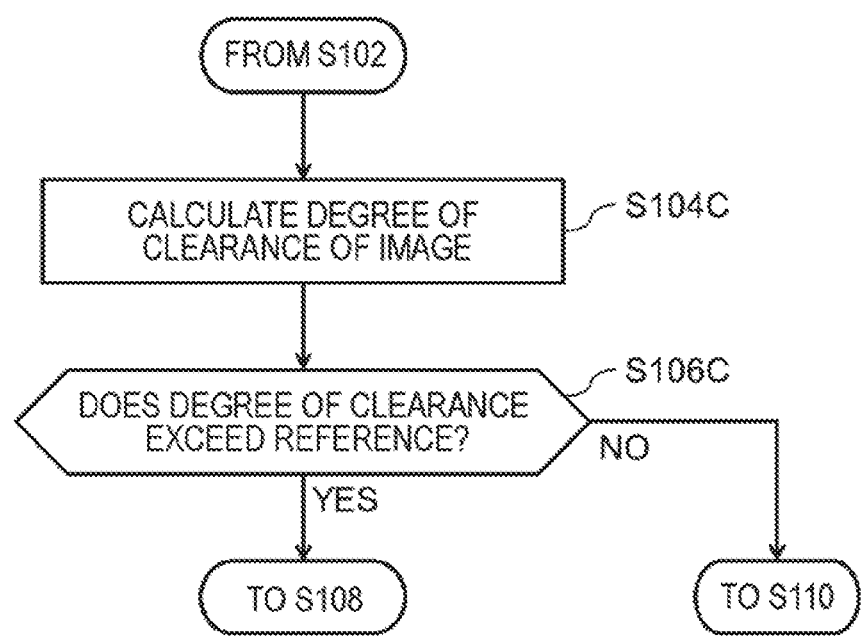
FIG. 7 is a flowchart illustrating a third specific example of the preprocessing executed by the first processing unit.

FIG. 7 is a flowchart illustrating a third specific example of the preprocessing which is executed by the first processing unit 110. In the specific example, the first processing unit 110 detects that "a degree of clearness of a subject, which is calculated from the input image, is equal to or less than a reference value" as the determination condition. For an unclear input image, it is not possible to properly acquire the feature value from the input image, and thus there is a possibility that accuracy of the judgment process is lowered. With respect to the image, it is possible to decide that the tumor judgment process is not necessary. On the other hand, for an input image, which is clear to some extent, it is possible to skillfully acquire the feature value from the input image, and thus it is possible to execute the judgment process with certain accuracy. With respect to the image, it is possible to decide that the tumor judgment process is necessary.

The first processing unit 110 calculates an index (hereinafter, expressed as "a clearness degree") which expresses the clearness of the input image acquired in S102 (S104C). The first processing unit 110 detects, for example, an area (pixel), in which shininess, halation, blown out highlights, blocked up shadows, and defocus, or the like is generated, of the input image in order to calculate the clearness degree of the input image. It is possible to detect an area where the shininess or the halation is generated using, for example, a technology or the like which is disclosed in a document below.

M. Arnold, A. Ghosh, S. Ameling, G. Lacey, "Automatic segmentation and inpainting of specular highlights for endoscopic imaging", Journal on Image and Video Processing, vol. 2010, no. 9, pp. 1-12, 2010.

In addition, it is possible to detect an area where the blown out highlights or the blocked up shadows are generated on the basis of, for example, a luminance value of each pixel. In addition, it is possible to detect an area where the defocus is generated on the basis of, for example, a spatial frequency, which is calculated through Fast Fourier Transform (FFT) or the like, of each pixel. It is possible for the first processing unit 110 to calculate a ratio of an area, which is detected as an area where the shininess, the halation, the blown out highlights, the blocked up shadows, the defocus, or the like is generated, to the whole area of the input image as the clearness degree of the input image.

Furthermore, the first processing unit 110 decides whether or not the clearness degree of the input image exceeds the reference on the basis of a result of the calculation in S104C (S106C). Specifically, the first processing unit 110 compares the clearness degree calculated in S104C with the reference value, which is previously maintained in the memory 103 or the like, for the clearness degree decision. In a case where the clearness degree calculated in S104C exceeds the reference value for the clearness degree decision, it is possible for the first processing unit 110 to decide that the input image acquired in S102 has a clearness degree to some extent and "the input image is suitable for the tumor judgment process". In a case where the clearness degree calculated in S104C is equal to or less than the reference value for the clearness degree decision, it is possible for the first processing unit 110 to decide that the input image acquired in S102 is not clear and "the input image is not suitable for the tumor judgment process".

A case where it is decided that "the clearness degree of the input image exceeds the reference" in the decision in S106C (S106C: YES) is, in other words, a case where the determination condition is not detected. In this case, the first processing unit 110 decides that "the tumor judgment process with respect to the first input image is necessary", and instructs the second processing unit 120 to execute the tumor judgment process with respect to the first input image. The second processing unit 120 executes the tumor judgment process with respect to the input images acquired in S102 according to the instruction (S108).

On the other hand, a case where it is decided that "the clearness degree of the input image is equal to or less than the reference value" in the decision in S106C (S106C: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

Fourth Specific Example

Figure 8:
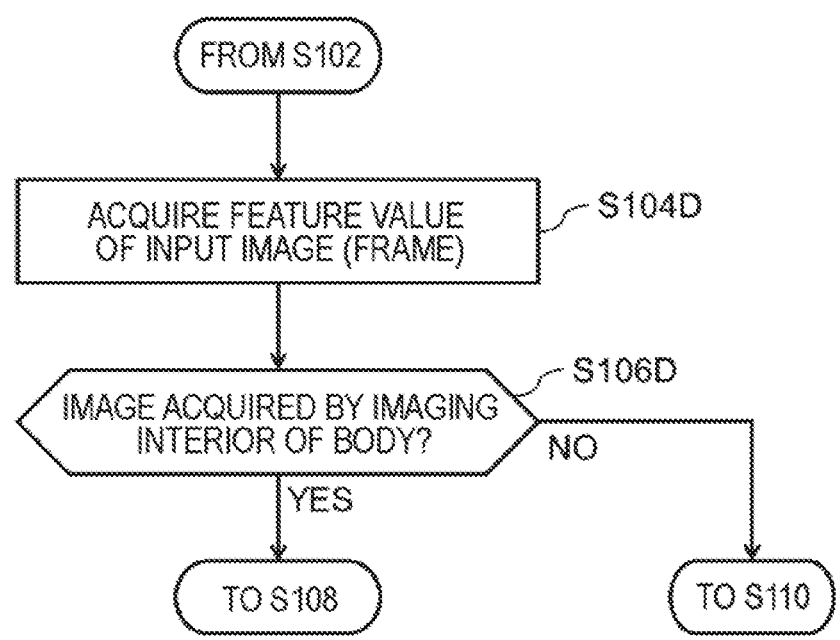
FIG. 8 is a flowchart illustrating a fourth specific example of the preprocessing executed by the first processing unit.

FIG. 8 is a flowchart illustrating a fourth specific example of the preprocessing which is executed by the first processing unit 110. In the specific example, the first processing unit 110 detects that "the input image is an image acquired by imaging an area other than the interior of the body" as the determination condition. For example, the input image, which is acquired by imaging the outside of the body, is acquired before the endoscope is inserted into the interior of the body, immediately after the endoscope is withdrawn from the interior of the body, or the like. With respect to the input image, it is possible to decide that the tumor judgment process is obviously not necessary. On the other hand, with respect to the input image, which is acquired by imaging the interior of the body, it is possible to decide that the tumor judgment process is necessary.

The first processing unit 110 acquires the feature value of the input image acquired in S102 (S104D). The first processing unit 110 acquires, for example, a color feature value or the edge feature value from the input image.

Furthermore, the first processing unit 110 decides whether or not the input image is the image which is acquired by imaging the interior of the body, on the basis of the feature value of the input image acquired in S104D (S106D). It is possible for the first processing unit 110 to judge whether or not the input image is the image which is acquired by imaging the interior of the body, on the basis of a basic color, which can be judged from the color feature value, of an object and a shape, which can be judged from the edge feature value, of the object.

A case where it is decided to be "the image which is acquired by imaging the interior of the body" in the decision in S106D (S106D: YES) is, in other words, a case where the determination condition is not detected. In this case, the first processing unit 110 decides "the tumor judgment process with respect to the first input image is necessary", and instructs the second processing unit 120 to execute the tumor judgment process with respect to the first input image. The second processing unit 120 executes the tumor judgment process with respect to the input images acquired in S102 according to the instruction (S108).

On the other hand, a case where it is decided to be "the image which is not acquired by imaging the interior of the body" in the decision in S106D (S106D: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

Fifth Specific Example

Figure 9:
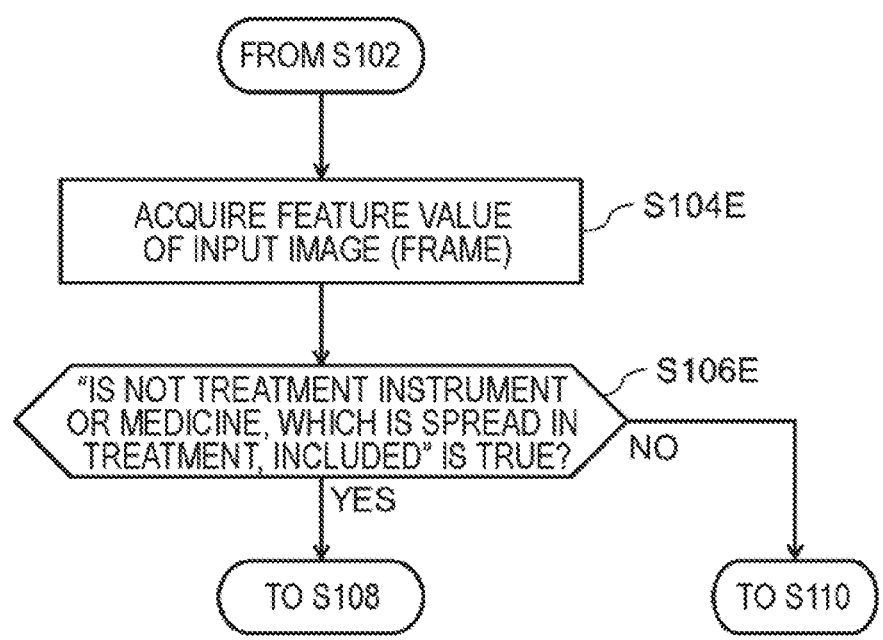
FIG. 9 is a flowchart illustrating a fifth specific example of the preprocessing executed by the first processing unit.

FIG. 9 is a flowchart illustrating a fifth specific example of the preprocessing which is executed by the first processing unit 110. In the specific example, the first processing unit 110 detects that "the input image is an image which includes an instrument used in a treatment with respect to the tumor or a medicine spread through the treatment" as the determination condition. In a case where the treatment instrument or the spread of the medicine is detected, it is possible to infer that the doctor already notices the tumor in the input image. With respect to the input image, it is not necessary to provide the information of the tumor to the doctor again, and thus it is possible to decide that the tumor judgment process is not necessary.

The first processing unit 110 acquires the feature value of the input image acquired in S102 (S104E). The first processing unit 110 acquires, for example, the color feature value or the edge feature value from the input image.

Furthermore, the first processing unit 110 decides whether or not the input image is the image which includes the treatment instrument or the spread medicine on the basis of the feature value of the input image acquired in S104E (S106E). It is possible for the first processing unit 110 to judge whether or not the treatment instrument exists by matching the basic color, which can be judged from the color feature value, of the object or the edge feature value with comparison data stored in the memory 103 or the like. In addition, it is possible to judge whether or not the medicine is spread on the basis of the basic color, which can be judged from the color feature value, of the object.

A case where it is decided that "the input image is not the image which includes the treatment instrument or the medicine spread in the treatment" in the decision in S106E (S106E: YES) is, in other words, a case where the determination condition is not detected. In this case, the first processing unit 110 decides that "the tumor judgment process with respect to the first input image is necessary", and instructs the second processing unit 120 to execute the tumor judgment process with respect to the first input image. The second processing unit 120 executes the tumor judgment process with respect to the input images acquired in S102 according to the instruction (S108).

On the other hand, a case where it is decided that "the input image is the image which includes the treatment instrument or the medicine spread in the treatment" in the decision in S106E (S106E: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

Sixth Specific Example

Figure 10:
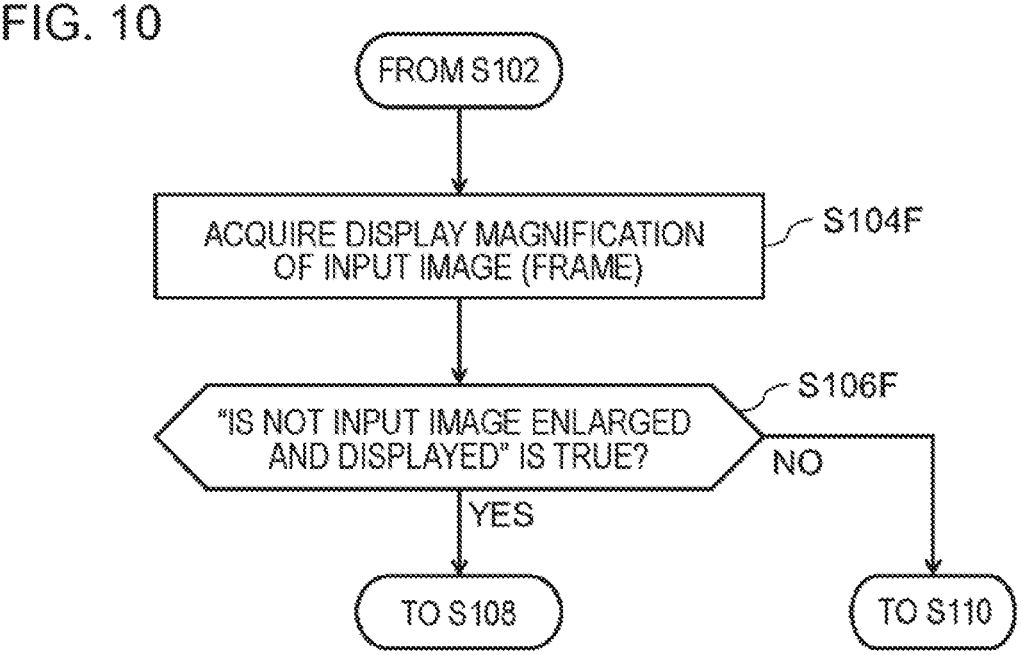
FIG. 10 a flowchart illustrating a sixth specific example of the preprocessing executed by the first processing unit.

FIG. 10 is a flowchart illustrating a sixth specific example of the preprocessing which is executed by the first processing unit 110. In the specific example, the first processing unit 110 performs detection while using a fact that "the input image is an image which is imaged after increasing a magnification" as the determination condition. In a case where the input image is enlarged and displayed, it is possible to decide that the doctor is diagnosing a range of the input image. With respect to the input image, it is possible to decide that the tumor judgment process is not necessary.

The first processing unit 110 acquires a display magnification of the input image acquired in S102 (S104F). It is possible for the first processing unit 110 to acquire the display magnification of the input image with reference to, for example, a property or the like of the input image.

Furthermore, the first processing unit 110 decides whether or not the input image acquired in S102 is enlarged and displayed on the basis of the display magnification acquired in S104F (S106F). Specifically, the first processing unit 110 compares a default display magnification, which is previously maintained in the memory 103 or the like, with the display magnification acquired in S104F. In a case where the display magnification acquired in S104F is equal to or larger than the default display magnification, it is possible for the first processing unit 110 to decide that the input image is enlarged and displayed.

A case where it is decided that "the input image is not enlarged and displayed" in decision in S106F (S106F: YES) is, in other words, a case where the determination condition is not detected. In this case, the first processing unit 110 decides that "the tumor judgment process with respect to the first input image is necessary", and instructs the second processing unit 120 to execute the tumor judgment process with respect to the first input image. The second processing unit 120 executes the tumor judgment process with respect to the input images acquired in S102 according to the instruction (S108).

On the other hand, in a case where it is decided that "the input image is enlarged and displayed" in the decision in S106F (S106F: NO) is, in other words, a case where the determination condition is detected. In this case, the first processing unit 110 decides that "the tumor judgment process with respect to the first input image is not necessary", skips the process in S108 of FIG. 4, and recognizes that "the diagnosis assistance information does not exist" (S110).

As described above, the number of times that the tumor judgment process, which is relatively slow in processing, is executed decreases according to the detection of the determination condition, and thus it is possible to reduce the whole throughput.

Second Example Embodiment

The example embodiment is the same as the first example embodiment other than the following points.

Functional Configuration

An image diagnosis apparatus 10 according to the example embodiment includes a functional configuration (for example: FIG. 2) which is the same as that of the first example embodiment. The first processing unit 110 of the example embodiment causes the threshold, which is used to decide the necessity of the tumor judgment process, to change according to the result of the tumor judgment process performed by the second processing unit 120.

For example, in a case where a positive result is acquired in the tumor judgment process performed by the second processing unit 120, it is possible for the image diagnosis apparatus 10 of the example embodiment to change a detection threshold of the determination condition in preprocessing thereafter in a direction in which a detection frequency of the determination condition increases.

As an example, in a case where the positive result is acquired in the tumor judgment process performed by the second processing unit 120, the first processing unit 110 may change the first threshold or the second threshold such that a reference range of the optical flow (movement vector) of the second processing unit 120 is enlarged. In a case where the reference range is enlarged, a frequency (a frequency in which it is decided that "the tumor judgment process is not necessary" with respect to the input image), in which the determination condition is detected, increases. In addition, as another example, the first processing unit 110 may increase, for example, the threshold which is set in relation to a ratio of the area where the shininess, the halation, the blown out highlights, the blocked up shadows, or defocus is generated. Therefore, the frequency (the frequency in which it is decided that "the tumor judgment process is not necessary" with respect to the input image), in which the determination condition is detected, increases. In addition, as another example, the first processing unit 110 may increase the reference value which is set with respect to a similarity degree of two input images. Therefore, the frequency (the frequency in which it is decided that "the tumor judgment process is not necessary" with respect to the input image), in which the determination condition is detected, increases.

In a case where the threshold is changed as described above, the tumor judgment process is skipped at a higher frequency. Therefore, it is possible to increase a throughput reduction effect.

In addition, in a case where a negative result is acquired in the tumor judgment process performed by the second processing unit 120, it is possible for the first processing unit 110 of the example embodiment to change the detection threshold of the determination condition in preprocessing thereafter in a direction in which the detection frequency of the determination condition decreases.

As an example, in a case where the negative result is acquired in the tumor judgment process performed by the second processing unit 120, the first processing unit 110 may change the first threshold or the second threshold such that the reference range of the optical flow (movement vector) of the second processing unit 120 is narrow. In a case where the reference range is narrow, the frequency (the frequency in which it is decided that "the tumor judgment process is not necessary" with respect to the input image), in which the determination condition is detected, decreases. In addition, as another example, the first processing unit 110 may reduce the threshold which is set with respect to, for example, the ratio of the area where the shininess, the halation, the blown out highlights, the blocked up shadows, or the defocus is generated. Therefore, the frequency (the frequency in which it is decided that "the tumor judgment process is not necessary" with respect to the input image), in which the determination condition is detected, decreases. In addition, as another example, the first processing unit 110 may reduce the reference value which is set with respect to the similarity degree of the two input images. Therefore, the frequency (the frequency in which it is decided that "the tumor judgment process is not necessary" with respect to the input image), in which the determination condition is detected, decreases.

In a case where the threshold is changed as described above, the tumor judgment process is executed with respect to a greater number of images. Therefore, an advantage is expected in which overlooking of the tumor is prevented from occurring in an input image (frame) after an input image (frame) in which a thing like the tumor is detected.

It should be noted that, the change of the above-described threshold may be executed for each frame, or may be executed in a case where the same judgment result is acquired a predetermined number of times in a plurality of frames in a fixed time.

Hardware Configuration of Image Diagnosis Apparatus 10

Similar to the first example embodiment, a hardware configuration of the image diagnosis apparatus 10 of the second example embodiment is illustrated, for example, with reference to FIG. 3. However, the storage device 104 of the image diagnosis apparatus 10 of the example embodiment further stores a program module which realizes the function of the image diagnosis apparatus 10 of the example embodiment.

Operation Example

Figure 11:
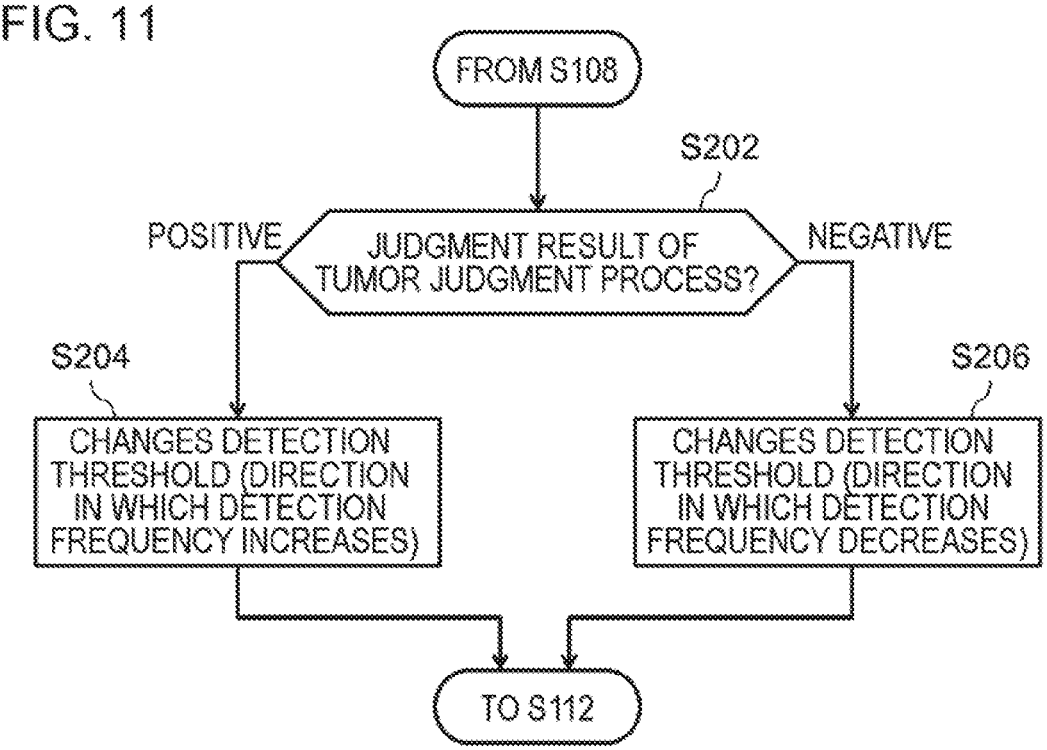
FIG. 11 is a flowchart illustrating a flow of a process performed by an image diagnosis apparatus according to a second example embodiment.

An operation example of the image diagnosis apparatus 10 of the example embodiment will be described with reference to FIG. 11. FIG. 11 is a flowchart illustrating a flow of a process performed by the image diagnosis apparatus 10 of the second example embodiment. The process in FIG. 11 is executed subsequent to, for example, S108 of FIG. 4.

The first processing unit 110 decides whether a judgment result of the tumor judgment process performed in S108 of FIG. 4 is positive or negative (S202). In a case where the judgment result of the tumor judgment process in S108 of FIG. 4 is positive (S202: positive), the first processing unit 110 changes the detection threshold of the determination condition in a direction in which the detection frequency of the determination condition increases (S204), as described above. On the other hand, in a case where the judgment result of the tumor judgment process in S108 of FIG. 4 is negative (S202: negative), the first processing unit 110 changes the detection threshold of the determination condition in a direction in which the detection frequency of the determination condition decreases (S206), as described above.

Hereinabove, according to the example embodiment, in a case where the positive result is acquired in the tumor judgment process with respect to a certain input image, a frequency, in which the tumor judgment process is executed on input images thereafter, increases, and thus it is possible to expect an advantage in that overlooking of the tumor is prevented from occurring. In addition, in a case where the negative result is acquired in the tumor judgment process with respect to the certain input image, the frequency, in which the tumor judgment process is executed on input images thereafter, decreases, and thus it is possible to increase an advantage in which the whole throughput decreases.

Third Example Embodiment

The example embodiment is the same as each of the above-described example embodiments other than the following points.

Functional Configuration

An image diagnosis apparatus 10 of the example embodiment includes a functional configuration (for example: FIG. 2) which is the same as that of the first example embodiment. In a case where it is decided that "the tumor judgment process is not necessary" through the preprocessing with respect to the certain input image (hereinafter, expressed as the "first input image"), the second processing unit 120 of the example embodiment uses the judgment result of the tumor judgment process with respect to the input image (hereinafter, expressed as the "second input image"), which is previous to the first input image, as the judgment result with respect to the first input image.

Hardware Configuration of Image Diagnosis Apparatus 10

A hardware configuration of the image diagnosis apparatus 10 of the third example embodiment is shown, for example, with reference to FIG. 3, similar to the first example embodiment. However, the storage device 104 of the image diagnosis apparatus 10 of the example embodiment further store a program module which realizes a function of the image diagnosis apparatus 10 of the example embodiment.

Operation Example

Figure 12:
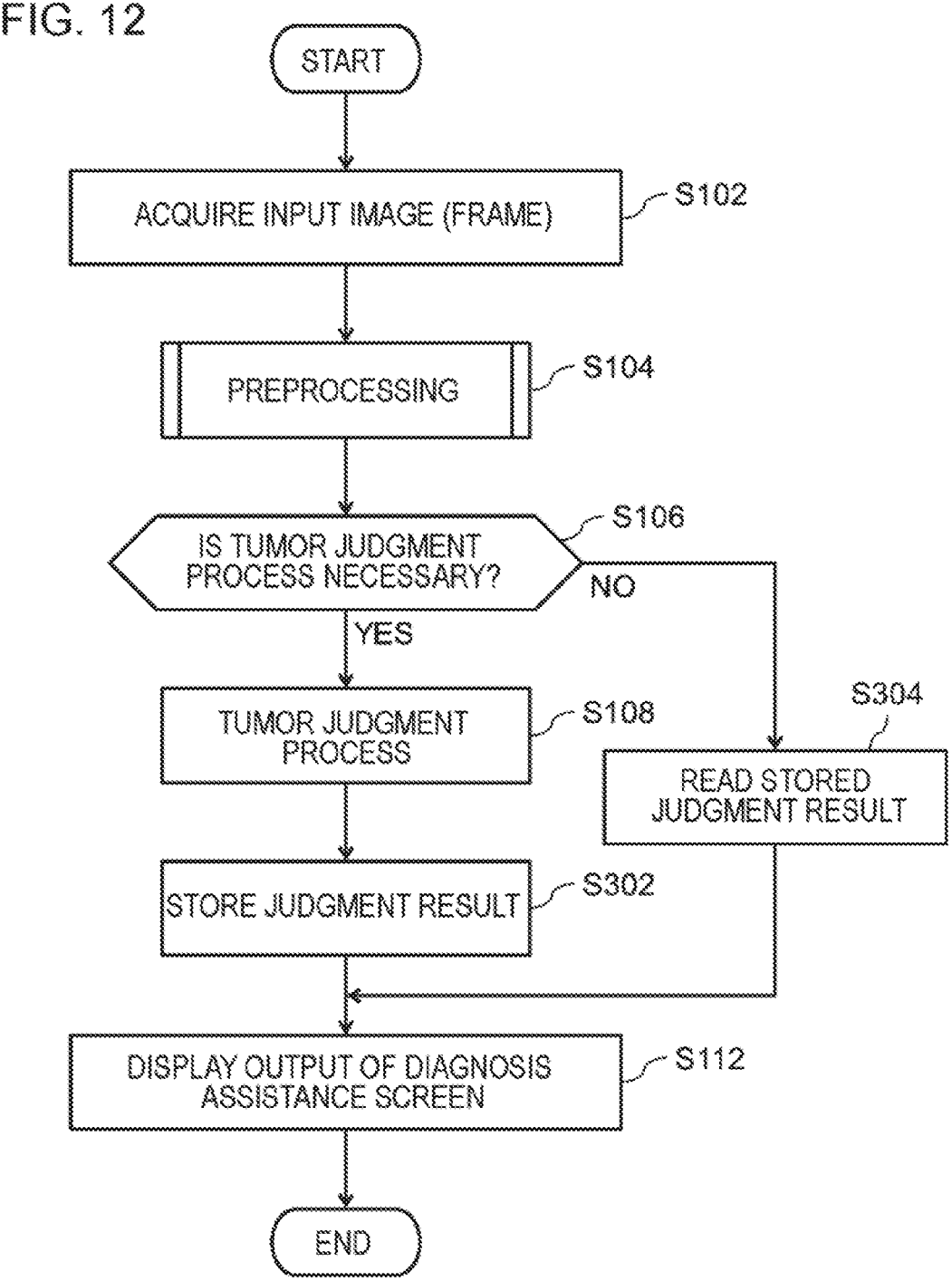
FIG. 12 is a flowchart illustrating a flow of a process performed by an image diagnosis apparatus according to a third example embodiment.

An operation example of the image diagnosis apparatus 10 of the example embodiment will be described with reference to FIG. 12. FIG. 12 is a flowchart illustrating a flow of a process performed by the image diagnosis apparatus 10 of the third example embodiment. Hereinafter, processes (S302 and S304) which are different from the first example embodiment will be mainly described. In addition, in an example of the drawing, description will be performed while it is assumed that the first input image and the second input image are frames which are sequential in time and the first input image is acquired after the second input image.

First, the second processing unit 120 stores the judgment result (diagnosis assistance information including positive/negative), which is acquired through the tumor judgment process with respect to the second input image, in a temporary storage area such as the memory 103 (S302).

Thereafter, in a case where it is decided that the tumor judgment process is not necessary with respect to the first input image acquired in the process in S102 (S106: NO), the second processing unit 120 reads a judgment result of the second input image which is stored in the temporary storage area, such as the memory 103, in the above-described process in S302 (S304). The second processing unit 120 uses the read judgment result of the second input image as a judgment result of the first input image for a process of display output of the diagnosis assistance screen in S112.

Hereinabove, in the example embodiment, in a case where it is decided that "the tumor judgment process is not necessary" as a result of the preprocessing with respect to the first input image, the result of the tumor judgment process with respect to the second input image, which is the immediately before frame of the first input image, is assumed as the result of the tumor judgment process with respect to the first input image. Therefore, it is possible to output the tumor judgment result with respect to an input image on which the tumor judgment process is not executed.

It should be noted that, for example, in a case where a frame rate of the image (moving image) imaged by the endoscope is 30 fps, elapsed time between two frames which are sequential in time is approximately 0.03 seconds. There is a low possibility that the imaging range of the endoscope is largely changed in the time. Therefore, even though a judgment result of the previous frame is applied to a subsequent frame, a large problem does not occur.

It should be noted that, although the sequential frames are described in the above-described example, the frames may be not necessarily sequential. For example, even between frames which are not sequential in fixed time, it is possible to apply the judgment result of the tumor judgment process with respect to frame in the past.

The specific example will be described with reference to FIG. 13. FIG. 13 is a diagram illustrating a modification example of the third example embodiment. FIG. 13 illustrates four frames (first to fourth frames). The first and second frames are images which are generated when the endoscope is inserted. In addition, the third and fourth frames are images which are generated when the endoscope is withdrawn.

Here, there is a case where images (similar images), which shows the same place of the interior of the body, are acquired in a case where the doctor repeats insertion/withdrawal of the endoscope during the diagnosis. In FIG. 13, the first and fourth frames and the second and third frames correspond to the images.

In an example of FIG. 13, it is assumed that the tumor judgment process is executed with respect to the first and second frames and a result thereof is stored in the memory 103 or the like, together with frame images. Thereafter, in a case where the third or fourth frame is acquired, the first processing unit 110 compares the third or fourth frame with each of the frame images stored in the memory 103.

The third frame has a similar relation with the second frame, and thus the first processing unit 110 decides that the tumor judgment process is not necessary with respect to the third frame. The second processing unit 120 receives a result of the decision, reads a judgment result of the tumor judgment process with respect to the second frame stored in the memory 103, and uses the judgment result as a judgment result with respect to the third frame.

In addition, the fourth frame has a similar relation with the first frame, and thus the first processing unit 110 decides that the tumor judgment process is not necessary with respect to the fourth frame. The second processing unit 120 receives a result of the decision, reads a judgment result of the tumor judgment process with respect to the first frame stored in the memory 103, and uses the judgment result as a judgment result with respect to the fourth frame.

As described above, even between frames which are not sequential, it is possible to apply a result of the tumor judgment process in the past. Therefore, it is possible to expect an effect in which the whole throughput decreases.

Hereinabove, although the example embodiments of the present invention are described with reference to the accompanying drawings, the example embodiments are only examples of the present invention, and it is possible to use a combination of the example embodiments or other various configurations.

What is claimed is:

1. An image diagnosis apparatus comprising:
a processor configured to:
execute preprocessing of judging whether or not a predetermined condition is detected in image processing with respect to at least one input image to decide whether or not a tumor judgment process is necessary with respect to each of a plurality of input images including the at least one input image, wherein the predetermined condition is a fact that the at least one input image includes any of an instrument used for a treatment with respect to a tumor and a medicine spread in the treatment; and
perform the tumor judgment process with respect to the at least one input image for which it is decided in the preprocessing that the tumor judgment process is necessary.

2. The image diagnosis apparatus according to claim 1, wherein the processor is further configured to detect that a difference between two successive input images, of the plurality of images, as frames, which are included in a moving image, is equal to or less than a reference value as the determination condition.

3. The image diagnosis apparatus according to claim 1, wherein the processor is further configured to detect at least one of a fact that an optical flow, which is calculated using the plurality of input images, is not included in a reference range, a fact that a degree of clearness, which is calculated from the at least one input image, of a subject is equal to or less than a reference value, a fact that the at least one input image is an image which is acquired by imaging an area other than an interior of a body, and a fact that the at least one input image is an image which is imaged with an increased magnification, as the determination condition.

4. The image diagnosis apparatus according to claim 1, wherein the processor is further configured to change a detection threshold of the determination condition in the preprocessing in a direction in which a detection frequency of the determination condition increases in a case where a positive result is acquired in the tumor judgment process performed.

5. The image diagnosis apparatus according to claim 1, wherein the processor is further configured to change a detection threshold of the determination condition in the preprocessing in a direction in which a detection frequency of the determination condition decreases in a case where a negative result is acquired in the tumor judgment process.

6. The image diagnosis apparatus according to claim 1, wherein the processor is further configured to use a judgment result of the tumor judgment process with respect to a second input image, which is previous to the at least one input image, as a judgment result with respect to the at least one input image in a case where it is decided that the tumor judgment process is not necessary through the preprocessing with respect to the first at least one input image.

7. The image diagnosis apparatus according to claim 6, wherein the at least one input image and the second input image are frames which are sequential in time.

8. The image diagnosis apparatus according to claim 1, wherein the processor is further configured to decide whether a result of the tumor judgment process is any of positive or negative on the basis of at least one of a color and a shape of a blood vessel which appears on an inside wall of an organ in the at least one input image.

9. The image diagnosis apparatus according to claim 1, wherein the processor is further configured to decide whether a result of the tumor judgment process is any of positive or negative on the basis of a shape of an inside wall of an organ in the at least one input image.

10. The image diagnosis apparatus according to claim 1, wherein the plurality of input images are frames which are included in a moving image generated using an endoscope.

11. An image diagnosis method, which is executed by a computer, the method comprising:
executing preprocessing of judging whether or not a predetermined condition is detected in image processing with respect to at least one input image to decide whether or not a tumor judgment process is necessary with respect to each of a plurality of input images including the at least one input image, wherein the predetermined condition is a fact that the at least one input image includes any of an instrument used for a treatment with respect to a tumor and a medicine spread in the treatment; and
performing the tumor judgment process with respect to the at least one input image for which it is decided in the preprocessing that the tumor judgment process is necessary.

12. The image diagnosis method according to claim 11, further comprising: detecting that a difference between two successive input images, of the plurality of images, as frames, which are included in a moving image, is equal to or less than a reference value as the determination condition.

13. The image diagnosis method according to claim 11, further comprising:
detecting at least one of a fact that an optical flow, which is calculated using the plurality of input images, is not included in a reference range, a fact that a degree of clearness, which is calculated from the at least one input image, of a subject is equal to or less than a reference value, a fact that the at least one input image is an image which is acquired by imaging an area other than an interior of a body, and a fact that the input image is an image which is imaged with an increased magnification, as the determination condition.

14. The image diagnosis method according to claim 11, further comprising:
changing a detection threshold of the determination condition in the preprocessing in a direction in which a detection frequency of the determination condition increases in a case where a positive result is acquired in the tumor judgment process.

15. The image diagnosis method according to claim 11, further comprising:
changing a detection threshold of the determination condition in the preprocessing in a direction in which a detection frequency of the determination condition decreases in a case where a negative result is acquired in the tumor judgment process.

16. The image diagnosis method according to claim 11, further comprising:
using a judgment result of the tumor judgment process with respect to a second input image of the plurality of images, which is previous to the at least one input image, as a judgment result with respect to the at least one input image in a case where it is decided that the tumor judgment process is not necessary through the preprocessing with respect to the at least one input image.

17. The image diagnosis method according to claim 16, wherein the at least one input image and the second input image are frames which are sequential in time.

18. The image diagnosis method according to claim 11, further comprising:
deciding whether a result of the tumor judgment process is any of positive or negative on the basis of at least one of a color and a shape of a blood vessel which appears on an inside wall of an organ in the at least one input image.

19. The image diagnosis method according to claim 11, further comprising:
deciding whether a result of the tumor judgment process is any of positive or negative on the basis of a shape of an inside wall of an organ in the at least one input image.

20. The image diagnosis method according to claim 11, wherein the plurality of input images are frames which are included in a moving image generated using an endoscope.

21. A non-transitory computer readable medium storing a program causing a computer to execute an image diagnosis method, the image diagnosis method comprising:
executing preprocessing of judging whether or not a predetermined condition is detected in image processing with respect to at least one input image to decide whether or not a tumor judgment process is necessary with respect to each of a plurality of input images including the at least one input image, wherein the predetermined condition is a fact that the at least one input image includes any of an instrument used for a treatment with respect to a tumor and a medicine spread in the treatment; and performing the tumor judgment process with respect to the at least one input image for which it is decided in the preprocessing that the tumor judgment process is necessary.

* * * * *